United States Patent
Ida

(10) Patent No.: US 9,442,062 B2
(45) Date of Patent: Sep. 13, 2016

(54) PHOTOACOUSTIC WAVE MEASUREMENT INSTRUMENT, PHOTOACOUSTIC WAVE MEASUREMENT DEVICE, METHOD, AND RECORDING MEDIUM

(71) Applicant: ADVANTEST CORPORATION, Tokyo (JP)

(72) Inventor: Taiichiro Ida, Gunma (JP)

(73) Assignee: ADVANTEST CORPORATION, Tokyo (JP)

( * ) Notice: Subject to any disclaimer, the term of this patent is extended or adjusted under 35 U.S.C. 154(b) by 306 days.

(21) Appl. No.: 14/219,650

(22) Filed: Mar. 19, 2014

(65) Prior Publication Data

US 2014/0307259 A1    Oct. 16, 2014

(30) Foreign Application Priority Data

Apr. 15, 2013   (JP) ................. 2013-084522

(51) Int. Cl.
| | |
|---|---|
| *G01H 9/00* | (2006.01) |
| *G01N 29/44* | (2006.01) |
| *G01N 21/17* | (2006.01) |
| *A61B 5/00* | (2006.01) |
| *G01N 29/24* | (2006.01) |
| *G01N 21/27* | (2006.01) |

(52) U.S. Cl.
CPC ......... *G01N 21/1702* (2013.01); *A61B 5/0095* (2013.01); *G01H 9/004* (2013.01); *G01N 21/274* (2013.01); *G01N 29/2418* (2013.01)

(58) Field of Classification Search
CPC ........... G01N 29/0609; G01N 29/221; G01N 29/2418; G01N 29/346; G01N 29/46; A61B 5/0095; A61B 5/489; A61B 5/68; G01H 9/00; G01H 9/004

USPC .................. 73/655, 602, 606, 645
See application file for complete search history.

(56) References Cited

U.S. PATENT DOCUMENTS

| | | | | |
|---|---|---|---|---|
| 5,070,733 A | * | 12/1991 | Nagata | G01N 29/0609 73/602 |
| 6,709,393 B2 | * | 3/2004 | Ogawa | A61B 5/0097 356/479 |
| 2005/0187471 A1 | * | 8/2005 | Kanayama | A61B 5/0091 600/437 |

(Continued)

FOREIGN PATENT DOCUMENTS

| | | |
|---|---|---|
| JP | 2004-286528 | 10/2004 |
| JP | 2008-267919 | 11/2008 |

(Continued)

OTHER PUBLICATIONS

U.S. Appl. No. 14/245,256 to Taiichiro IDA, filed Apr. 4, 2014.

(Continued)

*Primary Examiner* — Helen Kwok
(74) *Attorney, Agent, or Firm* — Greenblum & Bernstein, P.L.C.

(57) ABSTRACT

A photoacoustic wave measurement instrument includes a light output unit, a photoacoustic wave detection unit and a photoacoustic wave generation member. The light output unit outputs light. The photoacoustic wave detection unit receives a photoacoustic wave generated by the light in a measurement object, and converts the light into an electric signal. The photoacoustic wave generation member is arranged between an light output end of the light output unit and the measurement object, receives the light, and generates a known photoacoustic wave.

15 Claims, 15 Drawing Sheets

(56) References Cited

U.S. PATENT DOCUMENTS

| | | | |
|---|---|---|---|
| 2009/0066949 A1 | 3/2009 | Masumura | |
| 2011/0208057 A1* | 8/2011 | Oikawa | A61B 5/0095 600/443 |
| 2011/0319743 A1* | 12/2011 | Satoh | A61B 5/0095 600/407 |
| 2013/0121106 A1 | 5/2013 | Nishihara | |
| 2013/0131487 A1* | 5/2013 | Nagao | A61B 5/0095 600/407 |
| 2013/0205903 A1 | 8/2013 | Oyama | |
| 2013/0267823 A1* | 10/2013 | Nakajima | A61B 5/0095 600/407 |
| 2014/0100438 A1* | 4/2014 | Wada | A61B 5/0095 600/407 |
| 2014/0121505 A1* | 5/2014 | Irisawa | A61B 5/0095 600/424 |
| 2014/0251017 A1* | 9/2014 | Kandori | G01H 11/08 73/661 |
| 2014/0309515 A1* | 10/2014 | Ida | A61B 5/0095 600/407 |
| 2014/0309516 A1* | 10/2014 | Ida | A61B 5/0095 600/407 |
| 2015/0047433 A1* | 2/2015 | Ida | A61B 5/0095 73/645 |
| 2015/0075288 A1* | 3/2015 | Ida | A61B 5/0095 73/655 |
| 2015/0122036 A1* | 5/2015 | Ida | A61B 5/0095 73/655 |

FOREIGN PATENT DOCUMENTS

| | | |
|---|---|---|
| JP | 2009-68962 | 4/2009 |
| JP | 2010-125260 | 6/2010 |
| JP | 2012-24460 | 2/2012 |
| JP | 2012-105903 | 6/2012 |

OTHER PUBLICATIONS

U.S. Appl. No. 14/245,468 to Taiichiro Ida, filed Apr. 4, 2014.
Japan Office Action issued in Japan Patent Application No. 2013-84522, dated Jun. 30, 2016.

* cited by examiner upon Measurement upon Measurement

PHOTOACOUSTIC WAVE MEASUREMENT INSTRUMENT, PHOTOACOUSTIC WAVE MEASUREMENT DEVICE, METHOD, AND RECORDING MEDIUM

BACKGROUND OF THE INVENTION

1. Field of the Invention

The present invention relates to a photoacoustic sensor.

2. Related Art

Measurement of a measurement object by detecting photoacoustic waves has conventionally been known (refer to the following Patent Document 4, for example).

On this occasion, it is sometimes necessary to calibrate a photoacoustic sensor for detecting the photoacoustic wave. The photoacoustic sensor can be calibrated by irradiating light on a phantom including a target (it is assumed that an absorption characteristic of the light is known), detecting a photoacoustic wave, and comparing a detection result and a known absorption characteristic with each other.

PRIOR ART DOCUMENTS (Patent Document 1) Japanese Patent Application Laid-Open No. 2009-68962
(Patent Document 2) Japanese Patent Application Laid-Open No. 2004-286528
(Patent Document 3) Japanese Patent Application Laid-Open No. 2012-24460
(Patent Document 4) Japanese Patent Application Laid-Open No. 2012-105903

SUMMARY OF THE INVENTION

However, it is necessary to bring accurately the phantom into contact with the photoacoustic sensor via ultrasonic jerry, water, and the like in order to accurately calibrate the photoacoustic sensor.

It is therefore an object of the present invention to calibrate an error of a photoacoustic sensor without a phantom outside the photoacoustic sensor.

According to the present invention, a photoacoustic wave measurement instrument includes: a light output unit that outputs light; a photoacoustic wave detection unit that receives a photoacoustic wave generated by the light in a measurement object, and converts the light into an electric signal; and a photoacoustic wave generation member that is arranged between an light output end of the light output unit and the measurement object, receives the light, and generates a known photoacoustic wave.

According to the thus constructed photoacoustic wave measurement instrument, a light output unit outputs. A photoacoustic wave detection unit receives a photoacoustic wave generated by the light in a measurement object, and converts the light into an electric signal. A photoacoustic wave generation member is arranged between an light output end of the light output unit and the measurement object, receives the light, and generates a known photoacoustic wave.

According to the present invention, the photoacoustic wave measurement instrument may include a transmission member that is arranged between the light output end of the light output unit and the measurement object, and transmits the light and the photoacoustic wave, wherein the photoacoustic wave generation member is arranged inside or on the transmission member.

According to the photoacoustic wave measurement instrument of the present invention, the photoacoustic wave generation member may be arranged inside the transmission member.

According to the photoacoustic wave measurement instrument of the present invention, the photoacoustic wave generation member may be arranged on an outer peripheral surface of the transmission member.

According to the present invention, the photoacoustic wave measurement instrument may include a transmission member that is arranged between the light output end of the light output unit and the measurement object, and transmits the light and the photoacoustic wave, wherein the photoacoustic wave generation member is the transmission member.

According to the photoacoustic wave measurement instrument of the present invention, the photoacoustic wave generation member may be colored.

According to the photoacoustic wave measurement instrument of the present invention, the photoacoustic wave generation member may be mixed with a material which receives the light and generates the known photoacoustic wave.

According to the photoacoustic wave measurement instrument of the present invention, the light output unit may be an optical fiber.

According to the photoacoustic wave measurement instrument of the present invention, the photoacoustic wave detection unit may be a piezoelectric element.

According to the photoacoustic wave measurement instrument of the present invention, the transmission member may be a matching layer which matches acoustic impedances of the measurement object and the photoacoustic wave detection unit with each other.

According to the present invention, a photoacoustic wave measurement device for receiving an electric signal from the photoacoustic wave measurement instrument of the present invention, includes: a characteristic value recording unit that records a characteristic value of the known photoacoustic wave; an error measurement unit that compares a characteristic value of the photoacoustic wave generated by the photoacoustic wave generation member and the recorded content of the characteristic value recording unit with each other, and measures an error therebetween; and an error correction unit that corrects an error based on the error measured by the error measurement unit when the photoacoustic wave generated by the measurement object is measured.

The thus constructed photoacoustic wave measurement device receives an electric signal from the photoacoustic wave measurement instrument of the present invention. A characteristic value recording unit records a characteristic value of the known photoacoustic wave. An error measurement unit compares a characteristic value of the photoacoustic wave generated by the photoacoustic wave generation member and the recorded content of the characteristic value recording unit with each other, and measures an error therebetween. An error correction unit corrects an error based on the error measured by the error measurement unit when the photoacoustic wave generated by the measurement object is measured.

According to the photoacoustic wave measurement device of the present invention, the error correction unit may correct the error in the measurement result of the photoacoustic wave generated by the measurement object.

According to the photoacoustic wave measurement device of the present invention, the error correction unit may correct the error in the electric signal corresponding to the photoacoustic wave generated by the measurement object.

The present invention is a photoacoustic wave measurement method of measuring a photoacoustic wave by receiving an electric signal from a photoacoustic wave measurement instrument including a light output unit that outputs light; a photoacoustic wave detection unit that receives a photoacoustic wave generated by the light in a measurement object, and converts the light into an electric signal; and a photoacoustic wave generation member that is arranged between an light output end of the light output unit and the measurement object, receives the light, and generates a known photoacoustic wave, the method including: a characteristic value recording step that records a characteristic value of the known photoacoustic wave; an error measurement step that compares a characteristic value of the photoacoustic wave generated by the photoacoustic wave generation member and the recorded content of the characteristic value recording step with each other, and measures an error therebetween; and an error correction step that corrects an error based on the error measured by the error measurement step when the photoacoustic wave generated by the measurement object is measured.

The present invention is a computer-readable medium having a program of instructions for execution by a computer to perform a photoacoustic wave measurement process of a photoacoustic wave measurement device for receiving an electric signal from a photoacoustic wave measurement instrument including a light output unit that outputs light; a photoacoustic wave detection unit that receives a photoacoustic wave generated by the light in a measurement object, and converts the light into an electric signal; and a photoacoustic wave generation member that is arranged between an light output end of the light output unit and the measurement object, receives the light, and generates a known photoacoustic wave, the process including: a characteristic value recording step that records a characteristic value of the known photoacoustic wave; an error measurement step that compares a characteristic value of the photoacoustic wave generated by the photoacoustic wave generation member and the recorded content of the characteristic value recording step with each other, and measures an error therebetween; and an error correction step that corrects an error based on the error measured by the error measurement step when the photoacoustic wave generated by the measurement object is measured.

MODE FOR CARRYING OUT THE INVENTION

A description will now be given of an embodiment of the present invention referring to drawings.

Figure 1:
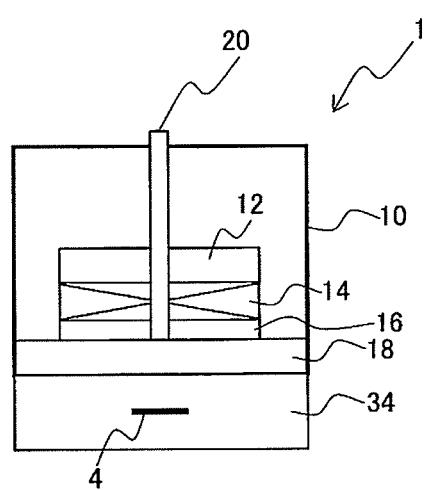
FIG. 1 is a cross sectional view of a photoacoustic wave measurement instrument 1 according to an embodiment of the present invention.

FIG. 1 is a cross sectional view of a photoacoustic wave measurement instrument 1 according to an embodiment of the present invention. The photoacoustic wave measurement instrument 1 includes a photoacoustic wave generation member 4, a case 10, a backing material 12, a piezoelectric element (photoacoustic wave detection unit) 14, electrodes 16, a spacer (transmission member) 18, an optical fiber (light output unit) 20, and an external spacer (transmission member) 34. The photoacoustic wave measurement instrument 1 is used for measuring the measurement object 2.

The case 10 is a case for storing the backing material 12, the piezoelectric element 14, the electrodes 16, and the spacer 18. The spacer 18 is in contact with a bottom surface of the case 10, the electrode 16 is placed on the spacer 18, the piezoelectric element 14 is placed on the electrode 16, and the backing material 12 is placed on the piezoelectric element 14. The backing material 12 is a lining material made of an epoxy resin, for example. The electrode 16 receives an electric signal (such as a voltage) from the piezoelectric element 14, and feeds the electric signal to the photoacoustic wave measurement device 40 (refer to FIG. 2). The electrode 16 is a gold electrode, for example.

The optical fiber (light output unit) 20 outputs light (such as pulse light P (refer to FIG. 5), but continuous light is conceivable) from a pulse output end (in contact with the spacer 18 in FIG. 1). It should be noted that the optical fiber 20 is connected to a pulse light source (not shown) external to the photoacoustic wave measurement instrument 1. The optical fiber 20 passes through the case 10, the backing material 12, the piezoelectric element 14, and the electrode 16.

The spacer 18 is arranged between the pulse light output end and the bottom surface of the case 10. The external spacer 34 is in contact with the case 10. The photoacoustic wave generation member 4 is arranged inside the external spacer (transmission member 34).

Figure 5:
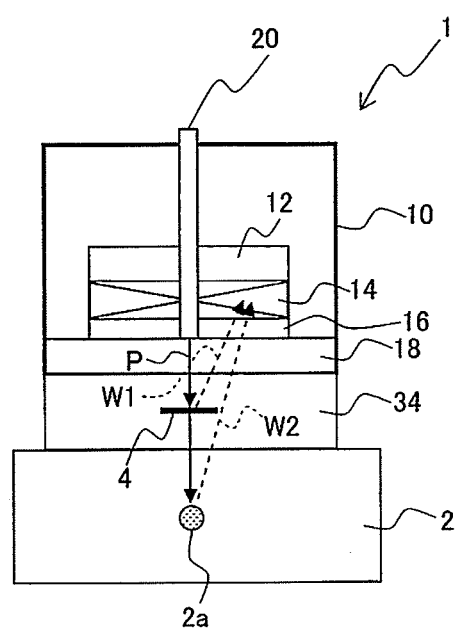
FIG. 5 is a cross sectional view of the photoacoustic wave measurement instrument 1 when the photoacoustic wave measurement instrument 1 is placed on the measurement object 2 for measurement.

FIG. 5 is a cross sectional view of the photoacoustic wave measurement instrument 1 when the photoacoustic wave measurement instrument 1 is placed on the measurement object 2 for measurement.

Referring to FIG. 5, the measurement object 2 is the finger cushion of the human, for example. Blood 2a in a blood vessel exists in the measurement object 2, and when the blood 2a in the blood vessel receives the pulse light P, the blood 2a generates a photoacoustic wave W2. The piezoelectric element 14 receives the photoacoustic wave W2, and converts the photoacoustic wave W2 into an electric signal (such as a voltage).

The piezoelectric element (photoacoustic wave detection unit) 14 receives a pressure of dilatational waves (photoacoustic waves W1 and W2) and converts the pressure into a voltage.

The spacer (transmission member) 18 transmits the pulse light P and the dilatational waves (photoacoustic waves W1 and W2), and is a transparent spacer made of acryl, epoxy, or quartz glass, for example. The spacer 18 is arranged between the pulse light output end and the measurement object 2. It should be noted that the spacer 18 may by an optical lens.

The external spacer (transmission member) 34 transmits the pulse light P and the dilatational waves (photoacoustic waves W1 and W2), and is arranged between the pulse light output end and the measurement object 2. It should be noted that the external spacer 34 is in contact with the case 10 and simultaneously the measurement object 2. The external spacer 34 is a transparent spacer made of acryl, epoxy, or quartz glass, for example.

It should be noted that the spacer 18 and the external spacer 34 are matching layers for transmitting the pulse light P and the dilatational waves (photoacoustic waves W1 and W2), thereby matching acoustic impedances of the measurement object 2 and the piezoelectric element 14 with each other.

Figure 3:
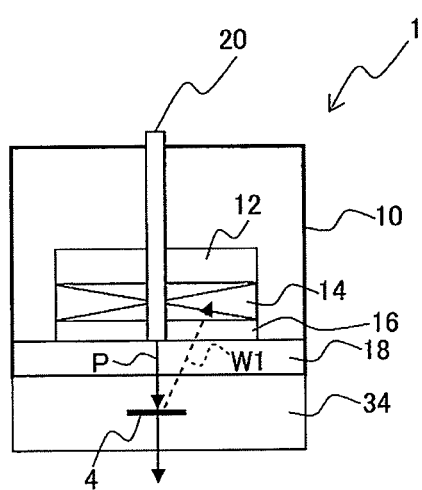
FIG. 3 is a cross sectional view of the photoacoustic wave measurement instrument 1 when the photoacoustic wave measurement instrument 1 is calibrated.

The photoacoustic wave generation member 4 is arranged in the external spacer (transparent member) 34, receives the pulse light P, and generates the known photoacoustic wave W1 (refer to FIGS. 3 and 5). It should be noted that the known photoacoustic wave W1 means that characteristic value (such as a time when a measurement result of the photoacoustic wave W1 reaches the peak, and the voltage of the peak) of the photoacoustic wave W1 is known. Moreover, the photoacoustic wave generation member 4 is arranged inside the external spacer (transmission member 34).

The photoacoustic wave generation member 4 slightly absorbs the pulse light P to such a degree as not to interfere with the measurement of the measurement object 2. For example, if the pulse light P is green laser light, the photoacoustic wave generation member 4 may be a light yellow ink.

Figure 2:
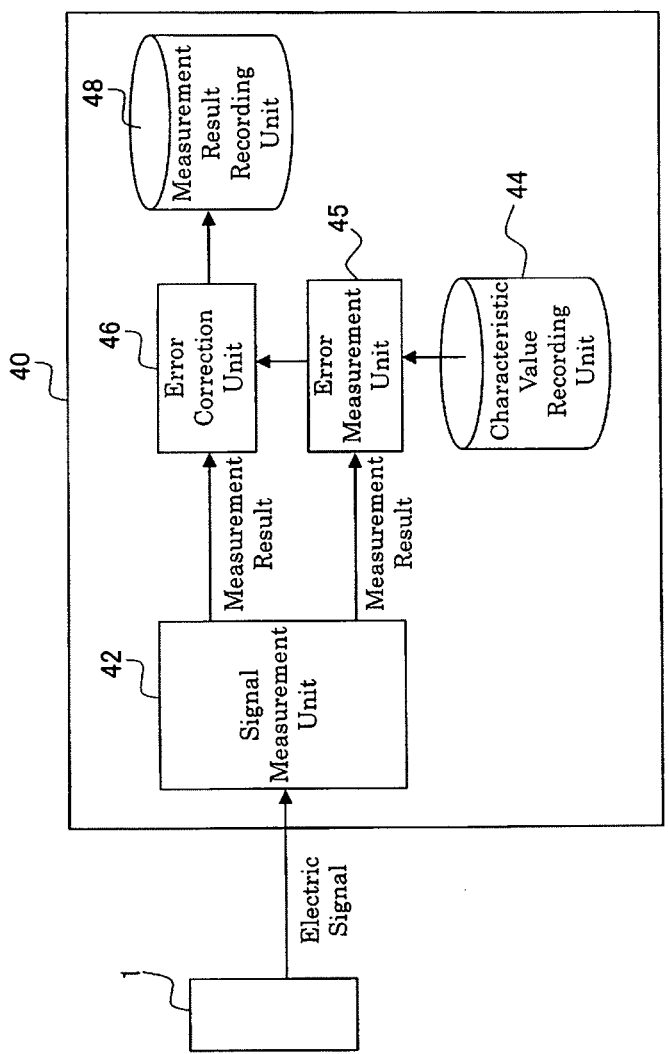
FIG. 2 is a functional block diagram showing a configuration of the photoacoustic wave measurement device 40 according to the embodiment of the present invention.

FIG. 2 is a functional block diagram showing a configuration of the photoacoustic wave measurement device 40 according to the embodiment of the present invention. The photoacoustic wave measurement device 40 is connected to the photoacoustic wave measurement instrument 1, and receives the electric signal (such as a voltage) output from the piezoelectric element 14 from the electrodes 16 of the photoacoustic wave measurement instrument 1.

The photoacoustic wave measurement device 40 includes a signal measurement unit 42, a characteristic value recording unit 44, an error measurement unit 45, an error correction unit 46, and a measurement result recording unit 48.

The signal measurement unit 42 measures the electric signal output from the piezoelectric element 14, and outputs a measurement result thereof (such as a relationship between the time and the voltage). Regarding the measurement result by the signal measurement unit 42, a measurement result for the photoacoustic wave W1 (refer to FIG. 3) generated by the photoacoustic wave generation member 4 is fed to the error measurement unit 45, and a measurement result for the photoacoustic wave W2 (refer to FIG. 5) generated by the measurement object 2 is fed to the error correction unit 46.

The characteristic value recording unit 44 records the characteristic value (such as the time when the measurement result of the photoacoustic wave W1 reaches the peak, and the voltage of the peak) of the known photoacoustic wave W1 (refer to FIG. 3).

The error measurement unit 45 compares the characteristic value (the measurement result by the signal measurement unit 42) of the photoacoustic wave W1 generated by the photoacoustic wave generation member 4 and the recorded content (which is the true value) of the characteristic value recording unit 44 with each other, thereby measuring an error therebetween.

The error correction unit 46 corrects an error when the photoacoustic wave W2 generated by the measurement object 2 is measured based on the error measured by the error measurement unit 45. In other words, the error in the measurement result (refer to FIG. 6) of the photoacoustic wave W2 generated by the measurement object 2 is corrected.

For example, it is assumed that the error measurement unit 45 recognizes that the measurement result of the characteristic value of the photoacoustic wave W1 (peak voltage and the timing thereof) is 1.1 times of and delayed by 30 ns from the true value. In this case, the error correction unit 46 multiplies the measurement result (the voltage and the time) of the photoacoustic wave W2 output from the signal measurement unit 42 by 1/1.1, and advances the measurement result by 30 ns.

The measurement result recording unit 48 records the measurement result of the photoacoustic wave W2 corrected by the error correction unit 46. It should be noted that an image of the measurement object 2 may be acquired and displayed based on the recorded content of the measurement result recording unit 48.

A description will now be given of an operation of the embodiment of the present invention.

(1) Operation in Calibration

FIG. 3 is a cross sectional view of the photoacoustic wave measurement instrument 1 when the photoacoustic wave measurement instrument 1 is calibrated.

First, the external pulse light source (not shown) generates the pulse light P, the pulse light P passes through the optical fiber 20, and the pulse light P is output from the pulse light output end. The pulse light P passes through the spacer 18, and is made incident to the external spacer 34. The photoacoustic wave generation member 4 is arranged inside the external spacer 34. Almost all of the pulse light P transmits through the photoacoustic wave generation member 4. However, the photoacoustic wave generation member 4 slightly absorbs the pulse light P, and generates the minute photoacoustic wave W1.

The photoacoustic wave W1 passes through the external spacer 34, the spacer 18, and the electrode 16, and reaches the piezoelectric element 14. The piezoelectric element 14 converts the pressure caused by the photoacoustic wave W1 into the electric signal (such as the voltage). The electric signal (such as the voltage) is extracted via the electrodes 16 to the outside, and is fed to the photoacoustic wave measurement device 40.

Figure 4:
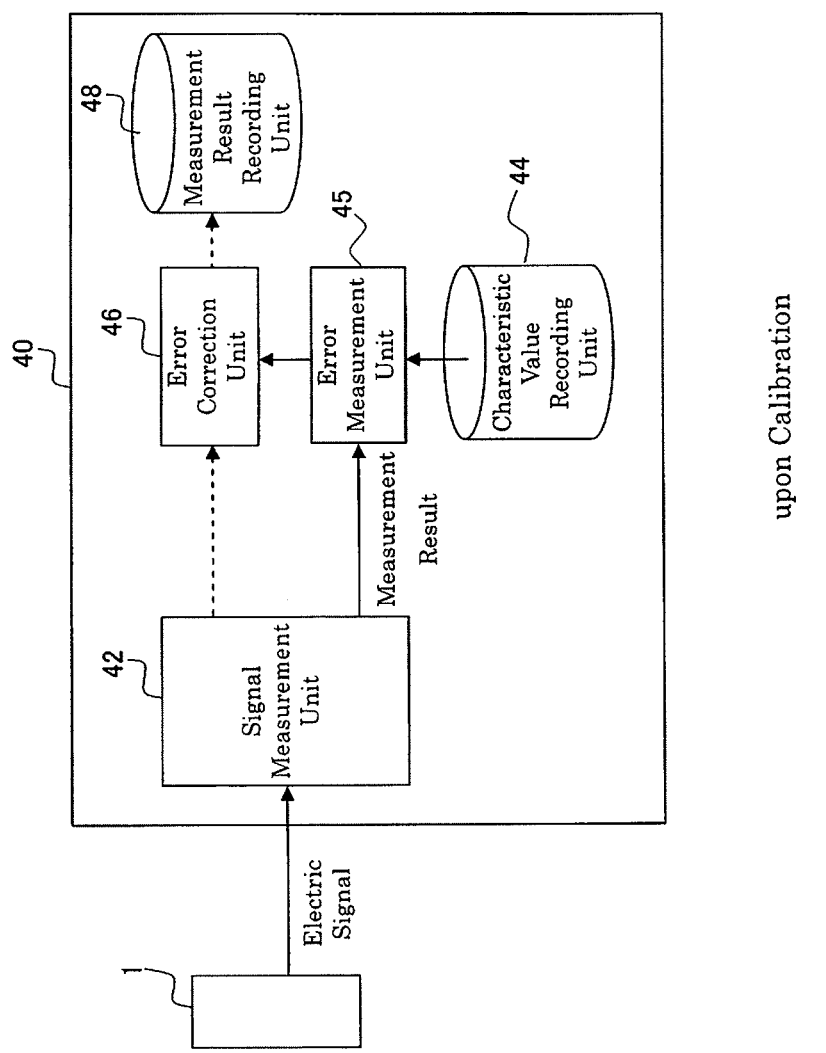
FIG. 4 is a diagram for describing an operation of the photoacoustic wave measurement device 40 when the photoacoustic wave measurement instrument 1 is calibrated.

FIG. 4 is a diagram for describing an operation of the photoacoustic wave measurement device 40 when the photoacoustic wave measurement instrument 1 is calibrated.

The electric signal output from the electrodes 16 of the photoacoustic wave measurement instrument 1 is fed to the signal measurement unit 42. The signal measurement unit 42 measures the fed electric signal. A measurement result by the signal measurement unit 42 is a measurement result relating to the photoacoustic wave W1 (refer to FIG. 3) generated by the photoacoustic wave generation member 4.

The measurement result by the signal measurement unit 42 is fed to the error measurement unit 45. It should be noted that the measurement result is the characteristic value (such as the time when the measurement result of the photoacoustic wave W1 reaches the peak, and the voltage of the peak), for example. Moreover, the error measurement unit 45 reads the characteristic value of the photoacoustic wave W1 recorded in the characteristic value recording unit 44.

The error measurement unit 45 compares the measurement result by the signal measurement unit 42 and the recorded content (true value) in the characteristic value recording unit 44 with each other, thereby measuring the error therebetween. The measured error is fed to the error correction unit 46. The error correction unit 46 determines a correction quantity for the error based on the measured error.

For example, it is assumed that the error measurement unit 45 recognizes that the measurement result of the characteristic value of the photoacoustic wave W1 (peak voltage and the timing thereof) is 1.1 times of and delayed by 30 ns from the true value. In this case, the error correction unit 46 determines the correction quantity for the error (multiplies the measurement result (voltage and time) of the photoacoustic wave W2 output from the signal measurement unit 42 by 1/1.1, and advances the measurement result by 30 ns) based on the situation, "1.1 times of and delayed by 30 ns of the true value", which represents the measured error.

(2) Operation in Measurement

As described above, FIG. 5 is the cross sectional view of the photoacoustic wave measurement instrument 1 when the photoacoustic wave measurement instrument 1 is placed on the measurement object 2 for measurement.

First, the external pulse light source (not shown) generates the pulse light P, the pulse light P passes through the optical fiber 20, and the pulse light P is output from the pulse light output end. The pulse light P passes through the spacer 18, and is made incident to the external spacer 34. The photoacoustic wave generation member 4 is arranged inside the external spacer 34. Almost all of the pulse light P transmits through the photoacoustic wave generation member 4. However, the photoacoustic wave generation member 4 slightly absorbs the pulse light P, and generates the minute photoacoustic wave W1.

The photoacoustic wave W1 passes through the external spacer 34, the spacer 18, and the electrode 16, and reaches the piezoelectric element 14. The piezoelectric element 14 converts the pressure caused by the photoacoustic wave W1 into the electric signal (such as the voltage). The electric signal (such as the voltage) is extracted via the electrodes 16 to the outside, and is fed to the photoacoustic wave measurement device 40.

Moreover, the pulse light P, which has passed through the photoacoustic wave generation member 4, transmits through the external spacer 34, and is fed to the measurement object 2.

The pulse light P reaches the blood 2a in the blood vessel of the measurement object 2. Then, the blood 2a inside the blood vessel absorbs the pulse light P. As a result, the dilatational wave (photoacoustic wave W2) is output from the blood 2a in the blood vessel.

The photoacoustic wave W2 passes through the measurement object 2, the external spacer 34, the spacer 18, and the electrode 16, and reaches the piezoelectric element 14. The piezoelectric element 14 converts the pressure caused by the photoacoustic wave W2 into the electric signal (such as the voltage). The voltage is extracted via the electrodes 16 to the outside, and is fed to the photoacoustic wave measurement device 40.

The photoacoustic wave W2 reaches the piezoelectric element 14 after the minute photoacoustic wave W1. As a result, the photoacoustic wave W2 and the minute photoacoustic wave W1 can be distinguished from each other. Moreover, the photoacoustic wave W2 is rather larger than the minute photoacoustic wave W1. As a result, the electric signal output from the piezoelectric element 14 can be considered not to relate to the minute photoacoustic wave W1, but to relate to the photoacoustic wave W2. Thus, an artifact by the photoacoustic wave W1 can be neglected when the image of the measurement object 2 is acquired and displayed based on the recorded content in the measurement result recording unit 48.

Figure 6:
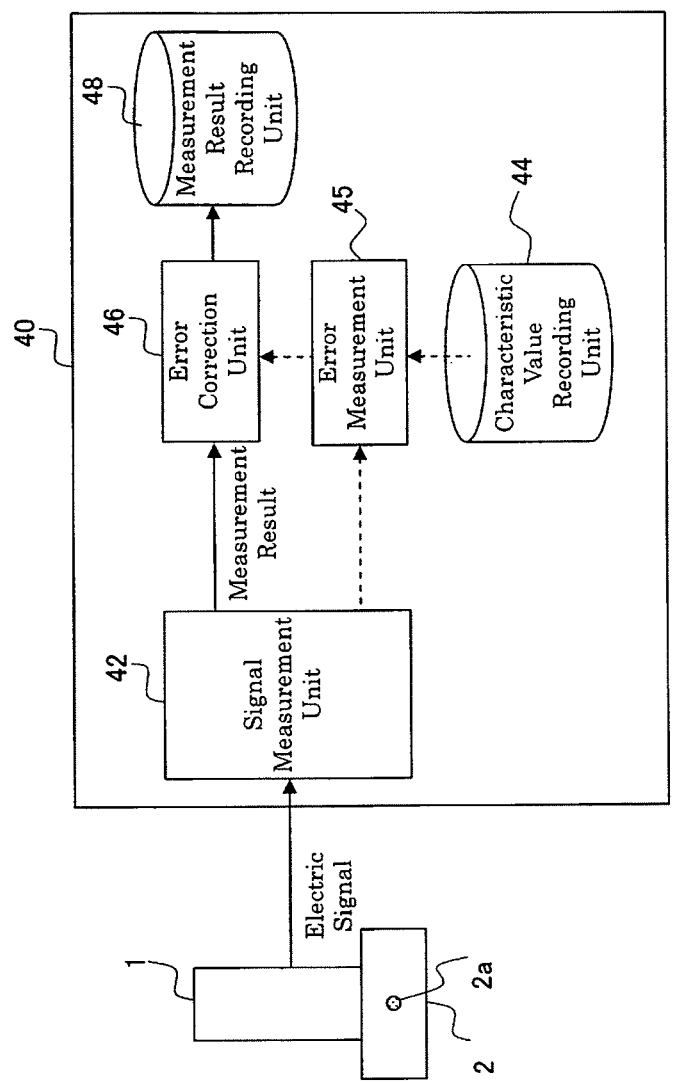
FIG. 6 is a diagram for describing the operation of the photoacoustic wave measurement device 40 when the photoacoustic wave measurement instrument 1 is placed on the measurement object 2 for measurement.

FIG. 6 is a diagram for describing the operation of the photoacoustic wave measurement device 40 when the photoacoustic wave measurement instrument 1 is placed on the measurement object 2 for measurement.

The electric signal output from the electrodes 16 of the photoacoustic wave measurement instrument 1 is fed to the signal measurement unit 42. The signal measurement unit 42 measures the fed electric signal. A measurement result by the signal measurement unit 42 is a measurement result relating to the photoacoustic wave W2 (refer to FIG. 5) generated by the measurement object 2.

The measurement result by the signal measurement unit 42 is fed to the error correction unit 46. It should be noted that the measurement result is the relationship between time and the voltage of the photoacoustic wave W2, for example. The error correction unit 46 corrects the measurement result according to the correction quantity (increase in voltage by 1/1.1 times, and advance in time by 30 ns, for example) of the error determined upon the calibration, and outputs the corrected measurement result to the measurement result recording unit 48.

The measurement result recording unit 48 records the measurement result of the photoacoustic wave W2 corrected by the error correction unit 46.

The correction of the error by the photoacoustic wave measurement instrument 1 can be carried out by means of the photoacoustic wave generation member 4 inside the photoacoustic wave measurement instrument 1 according to the embodiment of the present invention, resulting in elimination of necessity of using a phantom external to the photoacoustic wave measurement instrument 1. As a result, the correction of the error by the photoacoustic wave measurement instrument 1 can be carried out without an operation of bringing the phantom accurately in contact with the photoacoustic wave measurement instrument 1.

The error correction unit 46 corrects the error in the measurement result (refer to FIG. 6) of the photoacoustic wave W2 generated by the measurement object 2 according to the embodiment of the present invention. However, the error correction unit 46 may correct the error in the electric signal for the photoacoustic wave W2 generated by the measurement object 2.

Figure 7:
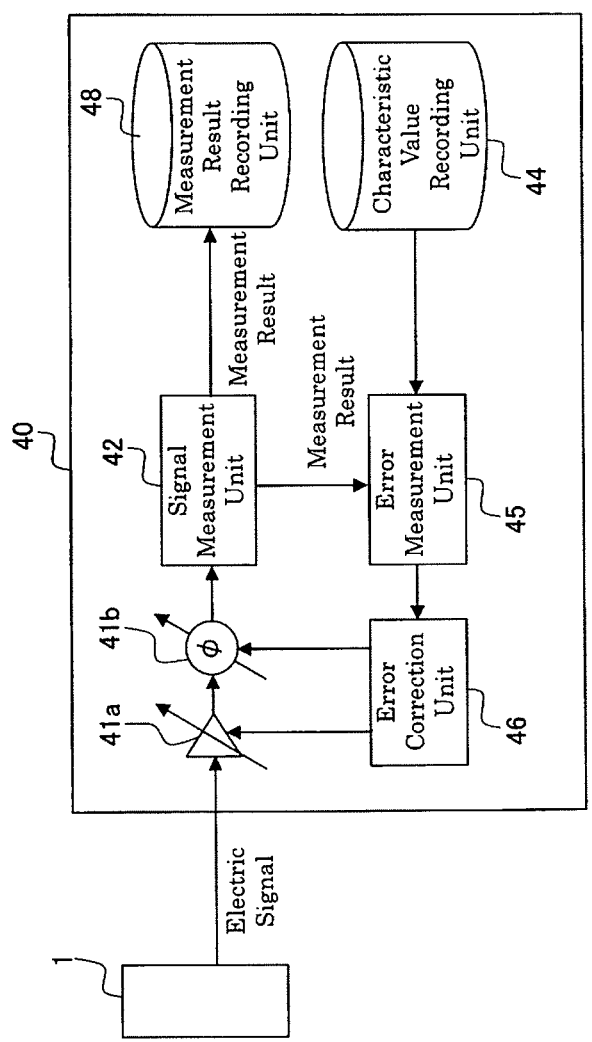
FIG. 7 is a functional block diagram showing a configuration of a variation of the photoacoustic wave measurement device 40.

FIG. 7 is a functional block diagram showing a configuration of a variation of the photoacoustic wave measurement device 40. The photoacoustic wave measurement device 40 according to the variation includes a variable amplifier 41a, a variable delay 41b, the signal measurement unit 42, the characteristic value recording unit 44, the error measurement unit 45, the error correction unit 46, and the measurement result recording unit 48.

The variable amplifier 41a amplifies or attenuates the electric signal output from the piezoelectric element 14. It should be noted that the gain of the variable amplifier 41a is variable. The variable delay 41b temporally delays the electric signal output from the piezoelectric element 14. How much the temporal delay is provided by the variable delay 41b is variable.

The signal measurement unit 42 receives and measures the electric signal output from the piezoelectric element 14 via the variable amplifier 41a and the variable delay 41b, and outputs a measurement result thereof (such as the relationship between the time and the voltage). Regarding the measurement result by the signal measurement unit 42, the measurement result for the photoacoustic wave W1 (refer to FIG. 3) generated by the photoacoustic wave generation member 4 is fed to the error measurement unit 45, and the measurement result for the photoacoustic wave W2 (refer to FIG. 5) generated by the measurement object 2 is fed to the measurement result recoding unit 48.

The characteristic value recording unit 44 and the error measurement unit 45 are the same as those according to the embodiment of the present invention.

The error correction unit 46 corrects an error in the electric signal for the photoacoustic wave W2 generated by the measurement object 2 based on the error measured by the error measurement unit 45. In other words, the error correction unit 46 corrects the error in the electric signal for the photoacoustic wave W2 by adjusting the gain of the variable amplifier 41a and the time delay of the variable delay 41b.

For example, it is assumed that the error measurement unit 45 recognizes that the measurement result of the characteristic value of the photoacoustic wave W1 (peak voltage and the timing thereof) is 1.1 times of and advanced by 30 ns from the true value. In this case, the error correction unit 46 multiplies the electric signal for the photoacoustic wave W2 output from the signal measurement unit 42 by 1/1.1 by means of the variable amplifier 41a, and delays by 30 ns by means of the variable delay 41b.

Moreover, though the photoacoustic wave generation member 4 is arranged inside the external spacer 34 according to this embodiment, various cases are conceivable as the position of the photoacoustic wave generation member 4.

Figure 8:
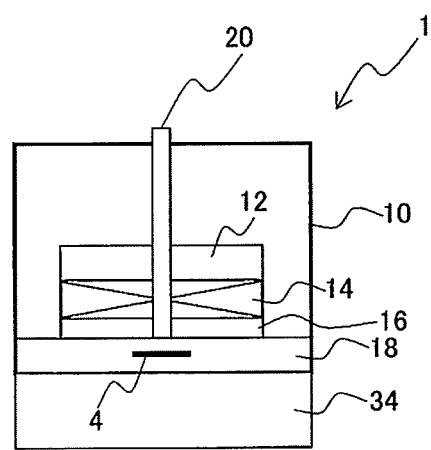
FIG. 8 is a cross sectional view of the photoacoustic wave measurement instrument 1 for a case where the photoacoustic wave generation member 4 is arranged inside the spacer 18.

FIG. 8 is a cross sectional view of the photoacoustic wave measurement instrument 1 for a case where the photoacoustic wave generation member 4 is arranged inside the spacer 18. As shown in FIG. 8, the photoacoustic wave generation member 4 may be arranged not inside the external spacer 34, but inside the spacer 18.

Moreover, the photoacoustic wave generation member 4 may be arranged on an outer peripheral surface of the transmission member (spacer 18 or the external spacer 34). For example, the photoacoustic wave generation member 4 is adhered to the outer peripheral surface of the transmission member.

Figure 9:
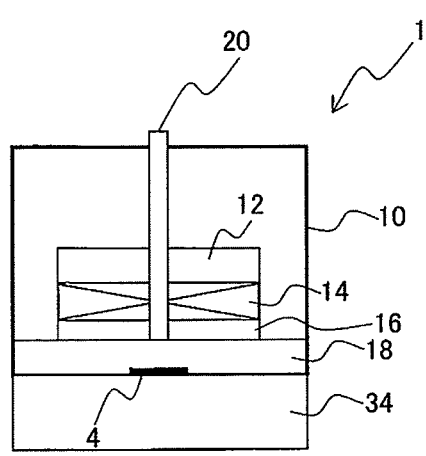
FIG. 9 is a cross sectional view of the photoacoustic wave measurement instrument 1 for a case where the photoacoustic wave generation member 4 is arranged on the outer peripheral surface of the spacer 18.

FIG. 9 is a cross sectional view of the photoacoustic wave measurement instrument 1 for a case where the photoacoustic wave generation member 4 is arranged on the outer peripheral surface of the spacer 18. Referring to FIG. 9, the photoacoustic wave generation member 4 may be arranged on the outer peripheral surface in contact with the bottom surface of the case 10 out of the outer peripheral surface of the spacer 18.

Figure 10:
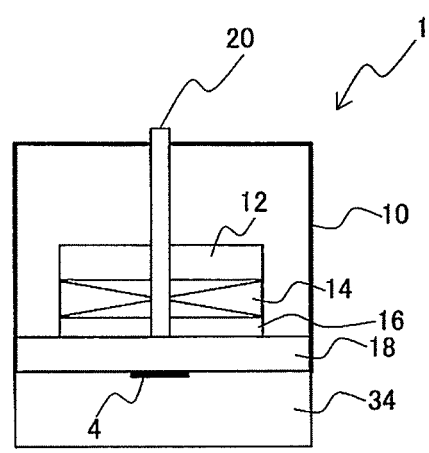
FIG. 10 is a cross sectional view of the photoacoustic wave measurement instrument 1 for a case where the photoacoustic wave generation member 4 is arranged on the outer peripheral surface of the external spacer 34.

FIG. 10 is a cross sectional view of the photoacoustic wave measurement instrument 1 for a case where the photoacoustic wave generation member 4 is arranged on the outer peripheral surface of the external spacer 34. Referring to FIG. 10, the photoacoustic wave generation member 4 may be arranged on the outer peripheral surface in contact with the bottom surface of the case 10 out of the outer peripheral surface of the external spacer 34.

Figure 11:
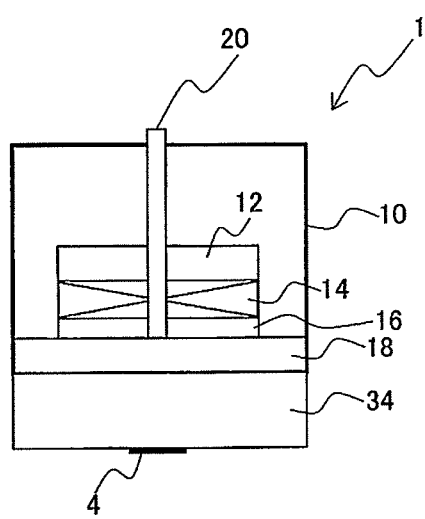
FIG. 11 is a cross sectional view of the photoacoustic wave measurement instrument 1 for a case where the photoacoustic wave generation member 4 is arranged on the outer peripheral surface of the external spacer 34.

FIG. 11 is a cross sectional view of the photoacoustic wave measurement instrument 1 for a case where the photoacoustic wave generation member 4 is arranged on the outer peripheral surface of the external spacer 34. Referring to FIG. 11, the photoacoustic wave generation member 4 may be arranged on the outer peripheral surface farthest from the bottom surface of the case 10 out of the outer peripheral surface of the external spacer 34.

Moreover, though the pulse light output end of the optical fiber 20 is in contact with the spacer 18 according to the embodiment of the present invention, the optical fiber 20 may pass through the spacer 18. In this case, the photoacoustic wave generation member 4 is arranged inside the external spacer 34 or on the outer peripheral surface of the external spacer 34.

Figure 12:
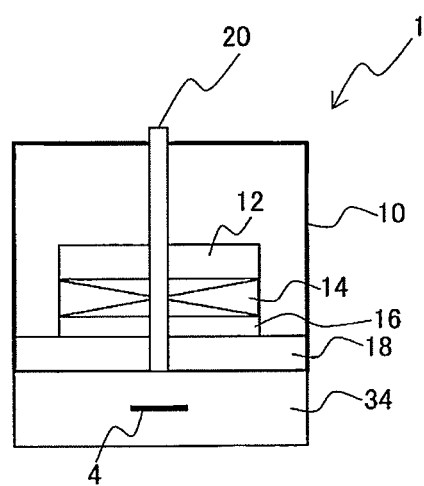
FIG. 12 is a cross sectional view of the photoacoustic wave measurement instrument 1 in the case where the optical fiber 20 passes through the spacer 18.

FIG. 12 is a cross sectional view of the photoacoustic wave measurement instrument 1 in the case where the optical fiber 20 passes through the spacer 18. Referring to FIG. 12, the photoacoustic wave generation member 4 may be arranged inside the external spacer 34.

Figure 13:
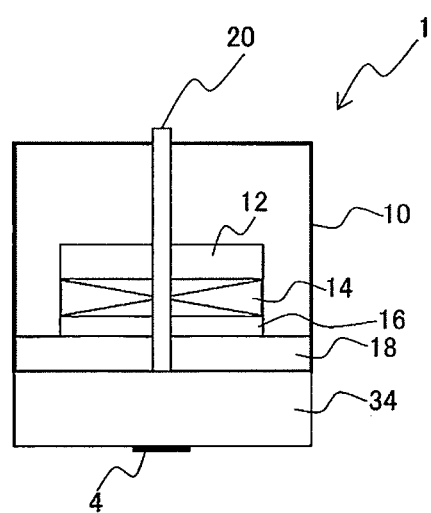
FIG. 13 is a cross sectional view of the photoacoustic wave measurement instrument 1 in the case where the optical fiber 20 passes through the spacer 18.

FIG. 13 is a cross sectional view of the photoacoustic wave measurement instrument 1 in the case where the optical fiber 20 passes through the spacer 18. Referring to FIG. 13, the photoacoustic wave generation member 4 may be arranged on the outer peripheral surface farthest from the bottom surface of the case 10 out of the outer peripheral surface of the external spacer 34.

A description has been given of the examples where the photoacoustic wave generation member 4 is arranged in or on the spacer 18 or the external spacer 34. However, the photoacoustic wave generation member 4 only needs to be arranged between the pulse light output end and the measurement object 2, and does not always need to be arranged in or on the spacer 18 or the external spacer 34.

Moreover, a description has been given of the examples where the photoacoustic wave generation member 4 is an independent member of the spacer 18 and the external spacer 34. However, either one or both of the spacer 18 and the external spacer 34 may function as the photoacoustic wave generation member 4. Even in this case, the spacer 18 and the external spacer 34 functioning as the photoacoustic wave generation member are still arranged between the pulse light output end and the measurement object 2.

Figure 14:
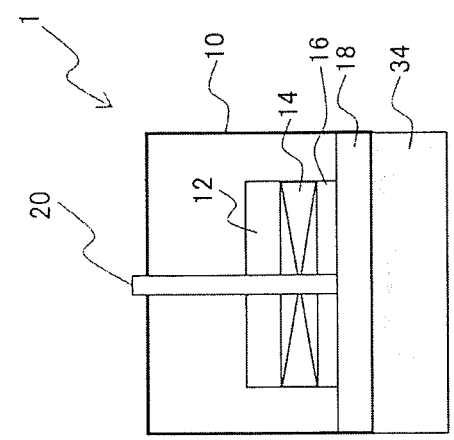
FIGS. 14(a)-14(c) include cross sectional views for a case where the external spacer 34 is colored (FIG. 14(a)), a case where the spacer 18 is colored (FIG. 14(b)), and a case where the external spacer 34 and the spacer 18 are colored (FIG. 14(c)) while the pulse output end of the optical fiber 20 is in contact with the spacer 18.
Figure 14:
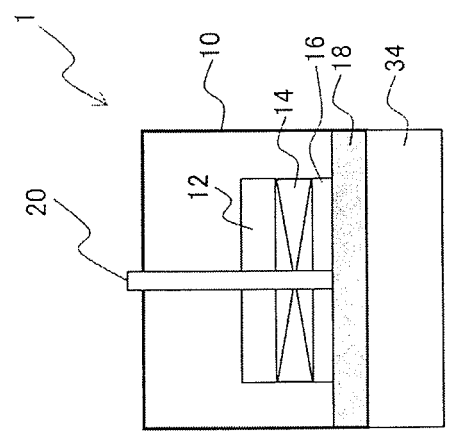
Figure 14:
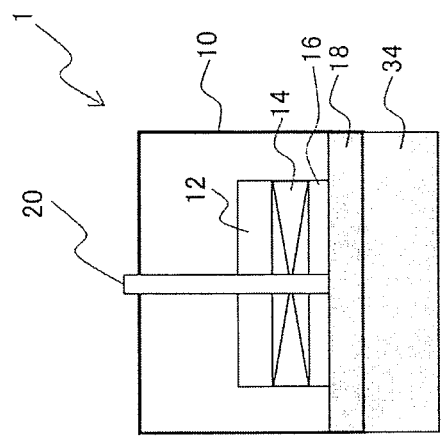

FIG. 14 includes cross sectional views for a case where the external spacer 34 is colored (FIG. 14(a)), a case where the spacer 18 is colored (FIG. 14(b)), and a case where the external spacer 34 and the spacer 18 are colored (FIG. 14(c)) while the pulse output end of the optical fiber 20 is in contact with the spacer 18.

Referring to FIG. 14(a), the external spacer 34 is so slightly colored as not to interfere with the measurement of the measurement object 2. As a result of the coloring, though most of the pulse light P transmits through the external spacer 34, a slight portion of the pulse light P is absorbed by the external spacer 34, and generates the known photoacoustic wave W1. For example, if the pulse light P is green laser light, it is conceivable to color the external spacer 34 in light yellow.

Referring to FIG. 14(b), the spacer 18 is so slightly colored as not to interfere with the measurement of the measurement object 2. As a result of the coloring, though most of the pulse light P transmits through the spacer 18, a slight portion of the pulse light P is absorbed by the spacer 18, and generates the known photoacoustic wave W1. For example, if the pulse light P is green laser light, it is conceivable to color the spacer 18 in light yellow.

Referring to FIG. 14(c), the external spacer 34 and the spacer 18 are so slightly colored as not to interfere with the measurement of the measurement object 2. As a result of the coloring, though most of the pulse light P transmits through the external spacer 34 and the spacer 18, a slight portion of the pulse light P is absorbed by the external spacer 34 and the spacer 18, and generates the known photoacoustic wave W1. For example, if the pulse light P is green laser light, it is conceivable to color the external spacer 34 and the spacer 18 in light yellow.

Figure 15:
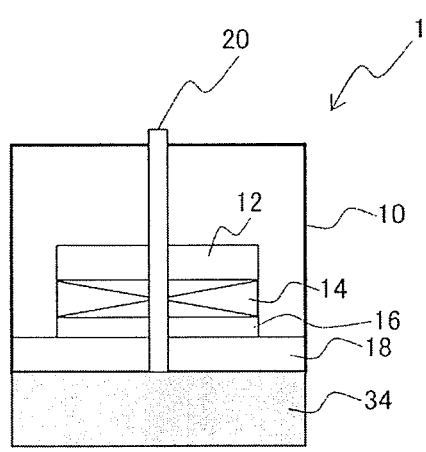
FIG. 15 is a cross sectional view of the photoacoustic wave measurement instrument 1 in a case where the pulse output end of the optical fiber 20 is in contact with the external spacer 34, and the external spacer 34 is colored.

FIG. 15 is a cross sectional view of the photoacoustic wave measurement instrument 1 in a case where the pulse output end of the optical fiber 20 is in contact with the external spacer 34, and the external spacer 34 is colored.

The external spacer 34 is so slightly colored as not to interfere with the measurement of the measurement object 2. As a result of the coloring, though most of the pulse light P transmits through the external spacer 34, a slight portion of the pulse light P is absorbed by the external spacer 34, and generates the known photoacoustic wave W1. For example, if the pulse light P is green laser light, it is conceivable to color the external spacer 34 in light yellow.

A description is given of the examples where either one or both of the spacer 18 and the external spacer 34 are colored, and are caused to function as the photoacoustic wave generation member referring to FIGS. 14 and 15. However, there are methods other than coloring so as to function either one or both of the spacer 18 and the external spacer 34 as the photoacoustic wave generation member. For example, it is conceivable to mix a material which receives the pulse light P, and generates the known photoacoustic wave W1 with either one or both of the spacer 18 and the external spacer 34. In this case, the pulse light P may be invisible.

Moreover, the above-described embodiment may be realized in the following manner. A computer is provided with a CPU, a hard disk, and a media (such as a floppy disk (registered trade mark) and a CD-ROM) reader, and the media reader is caused to read a medium recording a program realizing the above-described respective components such as the photoacoustic wave measurement device 40, thereby installing the program on the hard disk. This method may also realize the above-described functions.

What is claimed is:

1. A photoacoustic wave measurement instrument comprising:
    a light output unit that outputs light;
    a photoacoustic wave detection unit that receives a photoacoustic wave generated by the light in a measurement object, and converts the photoacoustic wave into an electric signal; and
    a photoacoustic wave generation member that is arranged between an light output end of the light output unit and the measurement object, receives the light, and generates a known photoacoustic wave.

2. The photoacoustic wave measurement instrument according to claim 1, comprising a transmission member that is arranged between the light output end of the light output unit and the measurement object, and transmits the light and the photoacoustic wave, wherein the photoacoustic wave generation member is arranged inside or on the transmission member.

3. The photoacoustic wave measurement instrument according to claim 2, wherein the photoacoustic wave generation member is arranged inside the transmission member.

4. The photoacoustic wave measurement instrument according to claim 2, wherein the photoacoustic wave generation member is arranged on an outer peripheral surface of the transmission member.

5. The photoacoustic wave measurement instrument according to claim 1, comprising a transmission member that is arranged between the light output end of the light output unit and the measurement object, and transmits the light and the photoacoustic wave, wherein the photoacoustic wave generation member is the transmission member.

6. The photoacoustic wave measurement instrument according to claim 5, wherein the photoacoustic wave generation member is colored.

7. The photoacoustic wave measurement instrument according to claim 5, wherein the photoacoustic wave generation member is mixed with a material which receives the light and generates the known photoacoustic wave.

8. The photoacoustic wave measurement instrument according to claim 1, wherein the light output unit is an optical fiber.

9. The photoacoustic wave measurement instrument according to claim 1, wherein the photoacoustic wave detection unit is a piezoelectric element.

10. The photoacoustic wave measurement instrument according to claim 2, wherein the transmission member is a matching layer which matches acoustic impedances of the measurement object and the photoacoustic wave detection unit with each other.

11. A photoacoustic wave measurement device for receiving an electric signal from the photoacoustic wave measurement instrument according to claim 1, comprising:
    a characteristic value recording unit that records a characteristic value of the known photoacoustic wave;
    an error measurement unit that compares a characteristic value of the known photoacoustic wave generated by the photoacoustic wave generation member with the recorded characteristic value, and measures an error between the characteristic value of the known photoacoustic wave generated by the photoacoustic wave generation member and the recorded characteristic value; and
    an error correction unit that corrects an error based on the error measured by the error measurement unit when the photoacoustic wave generated by the measurement object is measured.

12. The photoacoustic wave measurement device according to claim 11, wherein the error correction unit corrects the error in the photoacoustic wave generated by the measurement object.

13. The photoacoustic wave measurement device according to claim 11, wherein the error correction unit corrects the error in the electric signal corresponding to the photoacoustic wave generated by the measurement object.

14. A photoacoustic wave measurement method of measuring a photoacoustic wave by receiving an electric signal from a photoacoustic wave measurement instrument including a light output unit that outputs light; a photoacoustic wave detection unit that receives a photoacoustic wave generated by the light in a measurement object, and converts the photoacoustic wave into an electric signal; and a photoacoustic wave generation member that is arranged between an light output end of the light output unit and the measurement object, receives the light, and generates a known photoacoustic wave, the method comprising:
- a characteristic value recording step that records a characteristic value of the known photoacoustic wave;
- an error measurement step that compares a characteristic value of the known photoacoustic wave generated by the photoacoustic wave generation member with the recorded characteristic value, and measures an error between the characteristic value of the known photoacoustic wave generated by the photoacoustic wave generation member and the recorded characteristic value; and
- an error correction step that corrects an error based on the measured error when the photoacoustic wave generated by the measurement object is measured.

15. A computer-readable medium having a program of instructions for execution by a computer to perform a photoacoustic wave measurement process of a photoacoustic wave measurement device for receiving an electric signal from a photoacoustic wave measurement instrument including a light output unit that outputs light; a photoacoustic wave detection unit that receives a photoacoustic wave generated by the light in a measurement object, and converts the photoacoustic wave into an electric signal; and a photoacoustic wave generation member that is arranged between an light output end of the light output unit and the measurement object, receives the light, and generates a known photoacoustic wave, the process comprising:
- a characteristic value recording step that records a characteristic value of the known photoacoustic wave;
- an error measurement step that compares a characteristic value of the known photoacoustic wave generated by the photoacoustic wave generation member with the recorded characteristic value, and measures an error between the characteristic value of the known photoacoustic wave generated by the photoacoustic wave generation member and the recorded characteristic value; and
- an error correction step that corrects an error based on the measured error when the photoacoustic wave generated by the measurement object is measured.

* * * * *

UNITED STATES PATENT AND TRADEMARK OFFICE
CERTIFICATE OF CORRECTION

PATENT NO.         : 9,442,062 B2
APPLICATION NO.    : 14/219650
DATED              : September 13, 2016
INVENTOR(S)        : T. Ida Page 1 of 1

It is certified that error appears in the above-identified patent and that said Letters Patent is hereby corrected as shown below:

On the Title Page

Abstract (Line 8), please change "an light" to -- a light --.

In the Claims

At Column 12, Line 6 (Claim 1, Line 9), please change "an light" to -- a light --.

At Column 13, Line 13 (Claim 14, Line 9), please change "an light" to -- a light --.

At Column 14, Line 11 (Claim 15, Line 11), please change "an light" to -- a light --.

Signed and Sealed this
Second Day of May, 2017

Michelle K. Lee
*Director of the United States Patent and Trademark Office*